(12) United States Patent
Dominianni

(10) Patent No.: US 6,617,343 B1
(45) Date of Patent: Sep. 9, 2003

(54) HYPOGLYCEMIC N,N-ARYLSULFONYLGLYCINE COMPOUNDS

(75) Inventor: Samuel James Dominianni, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/069,033
(22) PCT Filed: Aug. 16, 2000
(86) PCT No.: PCT/US00/20779
§ 371 (c)(1), (2), (4) Date: May 7, 2002
(87) PCT Pub. No.: WO01/16119
PCT Pub. Date: Mar. 8, 2001

Related U.S. Application Data

(60) Provisional application No. 60/151,167, filed on Aug. 27, 1999.

(51) Int. Cl.[7] ............................................. A61K 31/42
(52) U.S. Cl. ...................... 514/374; 514/469; 548/236; 549/471
(58) Field of Search .................... 548/236; 549/471; 514/374, 469

(56) References Cited

FOREIGN PATENT DOCUMENTS

| EP | 0 769 498 | 4/1997 |
|---|---|---|
| EP | 0 947 500 | 10/1999 |
| JP | 04 099770 | 3/1992 |
| WO | WO 97 31910 | 9/1997 |

OTHER PUBLICATIONS

Sohda, et al., "Studies on Antidiabetic Agents. 11. Novel Thiazolidinedione derivatives as potent hypoglycemic and hypolipidemic agents," *Journal of Medicinal Chemistry*, vol. 35, No. 14, pp. 2617–2626 (1992).

J. Deruiter, et al., "N– and 2–substituted N– (phenylsulphonyl) glycines as inhibitors of rat lens aldose reductase," *Journal of Medicinal Chemistry*, vol. 32, No. 1, pp. 145–151 (1989).

A. Balsamo, et al., *Eur. J. Med. Chem.*, vol. 29, No. 10, pp. 787–794, (1994).

R. A. Davis, et al., J. *Enzyme Inhibition*, vol. 7, No. 2, pp. 87–96 (1993).

*Primary Examiner*—Joseph K. McKane
*Assistant Examiner*—Rei Shiao
(74) *Attorney, Agent, or Firm*—Francis O. Ginah; James J. Kelley

(57) ABSTRACT

A compound of formula 1:

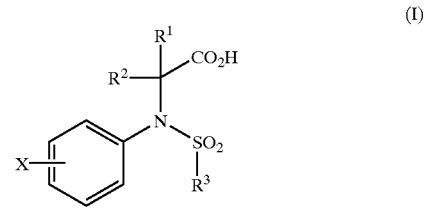

wherein, $R^1$, $R^2$ and $R^3$ independently represent hydrogen, alkyl, alkenyl, alkynyl, aryl, or aralkyl groups having 1 to 8 carbon atoms;

X represents an alkoxyalkyl, alkoxyaryl, alkoxyalkylaryl, aralkylalkoxy, or alkoxyalkylheterocycle; or a pharmaceutically acceptable salt or prodrug thereof.

9 Claims, No Drawings

HYPOGLYCEMIC N,N-ARYLSULFONYLGLYCINE COMPOUNDS

This application is a 371 of PCT/U.S. 00/20779 filed Aug. 16, 2000 which claims benefit of provisional application No. 60/151,167 filed Aug. 27, 1999.

FIELD OF THE INVENTION

The present invention relates to certain N,N-arylsulfonylglycine compounds, having utility as hypoglycemic agents, methods for their use, pharmaceutical compositions containing them and intermediates useful in their preparation.

BACKGROUND OF THE INVENTION

The disease, diabetes mellitus, is recognized in two forms. Type I diabetes requires exogenous insulin for control of the disease because it appears that endogenous production of insulin by the Isles of Langerhans in the pancreas is extremely poor or non-existent. Type I diabetes is often referred to as insulin-dependent diabetes mellitus (IDDM). Type II, non-insulin-dependent diabetes mellitus (NIDDM), is characterized by defects of insulin sensitivity in peripheral tissues such as adipose tissue and muscle, as described by J. E. Gerich in *New Engl. J. Med.*, 321, 1231–1245 (1989).

Hyperlipidemia is often observed in diabetics (*Diabetes Care*, 18, Supplement 1, 86–93, 1995). The combination of hyperlipidemia and hyperglycemia greatly increases the risk of cardiovascular diseases in diabetics. Successful treatment of hyperlipidemia and hyperglycemia in diabetics is needed urgently.

Blank reviewed hypoglycemic agents (*Burger's Medicinal Chemistry*, 4th Ed., Part II, John Wiley and Sons, N.Y., 1979, 1057–1080). Newer hypoglycemic agents were reviewed by Hulin in *Progress in Medicinal Chemistry*, 31, ed. G. P. Ellis and D. K. Luscombe, Elsevier Publishing Co., 1993.

Currently, partial control of NIDDM is achieved by a diet and exercise regimen, by administration of exogenous insulin, by administration of hypoglycemic agents, (e.g. the sulfonylureas), or by some combination of these protocols. Sulfonylureas, such as chloropropamide, acetohexamide and tolbutamide, are useful orally effective hypoglycemic agents achieving success in the control of NIDDM in numbers of patients. However, drugs currently available for the control of the hyperglycemia associated with type II diabetes mellitus (NIDDM) possess significant liabilities or limitations of efficacy. (Ellingboe, et al., *J. Med. Chem.* 36:2485–2493, 1993). Considerable effort has been expended toward developing novel, orally administered antihyperglycemic drugs. A preferred therapeutic approach for treating NIDDM incorporates drugs that counteract insulin resistance rather than those that stimulate endogenous insulin secretion. (J. R. Colca and D. R. Morton, *New Antidiabetic Drugs*, ed. C. J. Bailey and P. R. Flatt, Smith-Gordon and Company, Ltd., London, Chapter 24, 1990). Drugs that treat insulin resistance are called insulin sensitivity enhancers;

Sato, Y, et al. (*Diabetes Research and Clinical Practice*, 12:53–60, 1991) described the hypoglycemic effect of D-phenylalanine derivatives. In normal dogs, the hypoglycemic activity of the compound was greater than that of tolbutamide but less than that of glibenclamide. The compounds exerted a rapid hypoglycemic effect and improved glucose tolerance in genetically diabetic KK mice and in streptozotocin-treated rats. Yamasaki, et al. disclosed a group of 2-quinolone derivatives showing antidiabetic activity in NIDDM (WO 92/21342).

Hypoglycemic agents have been reviewed; references to earlier reviews, together with a review of newer agents, are to be found in Hulin [*Progress in Medicinal Chemistry*, Vol. 31, ed. By G. P. Ellis and D. K. Luscombe, Elsevier Publishing Co. (1993)].

Naphthalene sulfonamides containing amino acid moieties have been described as selective synthetic thrombin inhibitors (*Eur. J. Med. Chem.* (1988), 26 (6), 577–585). Some arylsulfonyl derivatives of substituted indoline-2-carboxamides were disclosed in EP 92-402213, published Aug. 03, 1992, as oxytocin and vasopressin antagonists. Aryl (but not alkyl) sulfonamides of N-aryl glycine derivatives, containing a rhodanine moiety, were disclosed as aldose reductase inhibitors for the treatment of diabetic complications (see JP 04099770 A2; published Mar. 31, 1992).

In view of these precedents, the observation of hypoglycemic activity in the object compounds of the present invention is novel and unexpected.

SUMMARY OF THE INVENTION

The present invention provides N,N-arylsulfonyylglycines useful in the treatment of hyperglycemia and/or hyperlipidemia.

The present invention provides a method of use of N,N-arylsulfonylglycines in the treatment of hyperglycemia and/or hyperlipidemia.

The present invention also provides a pharmaceutical composition containing N,N-arylsulfonylglycines useful for the treatment of non-insulin dependent diabetes mellitus (NIDDM).

The present invention relates to novel N,N-arylsulfonylglycine compounds of formula I:

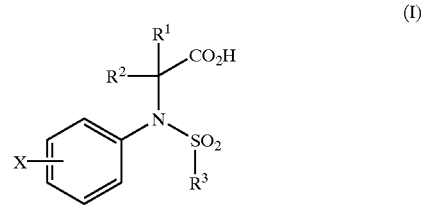

wherein, $R^1$ and $R^2$ are independently selected from hydrogen, alkyl, alkenyl, alkynyl, aryl, or aralkyl;

$R^3$ is selected from alkyl, alkenyl, alkynyl, aryl, aralkyl heteroaryl, or heteroaralkyl fragments of 1 to 8 carbon atoms with or without substituents;

X is a group selected from alkoxyalkyl, alkoxyaryl, alkoxyalkylaryl, aralkylalkoxy, alkoxyalkylheterocycle optionally substituted with alkyl, aryl, alkylaryl, aralkyl, heteroaryl, or heteroaralkyl fragments of 1 to 8 carbon atoms with or without substituents, attached to the aromatic ring ortho, meta, or para to the nitrogen substituent, or fused directly to any side of the aromatic ring, with or without additional fusion to the aromatic ring or pharmaceutically acceptable salts thereof.

This invention relates to a compound of formula I:

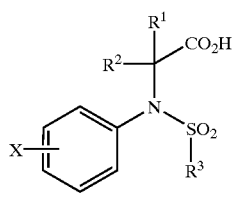

(I)

wherein,
$R^1$, $R^2$, and $R^3$ independently represent hydrogen, alkyl, alkenyl, alkynyl, aryl, or aralkyl groups having 1 to 8 carbon atoms;
X represents an alkoxyalkyl, alkoxyaryl, alkoxyalkylaryl, aralkylalkoxy, or alkoxyalkylheterocycle; or a pharmaceutically acceptable salt or prodrug thereof.

The present invention also provides a compound depicted by formula II:

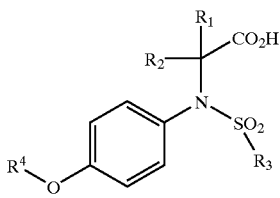

II wherein,
$R^1$, $R^2$, and $R^3$ are as described for formula I and and $R^4$ is a group selected from aryl, aralkyl, alkyaryl, alkyl heterocyclic, alkylarylheterocyclic, or a pharmaceutically acceptable salt thereof.

DETAILED DESCRIPTION OF THE INVENTION

The terms used to describe the instant invention have the following meanings herein.

A "mammal" is an individual animal that is a member of the taxonomic class mammalia. The class mammalia includes humans, monkeys, chimpanzees, gorillas, cattle, swine, horses, sheep, dogs, cats, mice, and rats.

"$C_{1-4}$ alkyl" refers to a straight or branched alkyl radicals having 1 to 4 carbon atoms, for example, methyl, ethyl, n-propyl, isopropyl, n-butyl, sec-butyl, or t-butyl.

"$C_{1-4}$ alkoxy" refers to a straight or branched chain alkyl radicals attached to oxygen having 1 to 4 carbon atoms, for example, methoxy, ethoxy, n-propoxy, isopropoxy, or t-butoxy, and the like.

The terms "active ingredient" and "active compound" as used herein are synonymous and refer to a compound(s) of the present invention as represented by formula I or its pharmaceutically acceptable salts or prodrug individually contained or combined with other compound(s) of formula I in a formulation of the invention. "Aryl" refers to a substituted or unsubstituted aromatic radical selected from the group consisting of 2-furyl, 3-furyl, 2-thienyl 3-thienyl, 1-pyrrolyl, 2-pyrrolyl, 3-pyrrolyl, phenyl, 2-pyridyl, 3-pyridyl, 4-pyridyl, 1-naphthyl, 2-naphthyl, 2-benzofuryl, 3-benzofuryl, 4-benzofuryl, 5-benzofuryl, 6-benzofuryl, 7-benzofuryl, 2-benzothieny, 3-benzothienyl, 4-benzothienyl, 5-benzothienyl, 6-benzothienyl, 7-benzothienyl, 1-indolyl, 2-indolyl, 3-indolyl, 4-indolyl, 5-indolyl, 6-indolyl and 7-indolyl. Aryl groups may be optionally substituted at one or two carbon atoms of the aryl group, and may be with $C_{1-4}$ alkyl, $C_{1-4}$ alkoxy, halogen—$NO_2$—CN—COOH—$CONH_2$—$SO_3H$, —$SO_2NH_2$ or trifluoromethyl. Examples of substituted aryl groups are 4-methyl-3-furyl, 3,4-dimethyl-2-thienyl, 2,4-dimethyl-3-thienyl, 3-ethoxy-4-methyl-2-benzofuryl, 2-cyano-3-benzofuryl, 4-trifluoromethyl-2-benzothienyl, 2-chloro-3-benzothienyl, 3,4-dichloro-2-pyridyl, 2-bromo-3-pyridyl, 2-fluoro-4-pyridyl, 4-fluoro-2-furyl, 2-carboxyphenyl, 4-carboxamidophenyl, 3-trifluoromethylphenyl, 2-bromo-1-naphthyl, 2,3-dimethyl-1-naphthyl, 3-carboxy-2-naphthyl, 5-carboxy-8-chloro-l-naphthyl, 3-ethyl-2-furyl, 8-fluoro-2-naphthyl, 5-trifluoromethyl-2-naphthyl, 6-ethoxy-2-naphthyl, 6,7-dimethoxy-2-naphthyl, 3-carboxy-2-naphthyl, and the like.

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, n-pentyl, and n-hexyl.

The term, "alkenyl" employed alone or in combination with other terms means a straight chain or branched monovalent hydrocarbon group having the stated number range of carbon atoms, and typified by groups such as vinyl, propenyl, crotonyl, isopentenyl, and various butenyl isomers.

The term, "hydrocarbyl" means an organic group containing only carbon and hydrogen.

The term, "halo" means fluoro, chioro, bromo, or iodo.

The term, "heterocyclic radical", refers to radicals derived from monocyclic or polycyclic, saturated or unsaturated, substituted or unsubstituted heterocyclic nuclei having 5 to 14 ring atoms and containing from 1 to 5 hetero atoms selected from the group consisting of nitrogen, oxygen or sulfur. Typical heterocyclic radicals are pyrrolyl, furanyl, thiophenyl, pyrazolyl, imidazolyl, triazolyl, isoxazolyl, oxazolyl, thiazolyl, thiadiazolyl, indolyl, carbazolyl, norharmanyl, azaindolyl, benzofuranyl, dibenzofuranyl, thianaphtheneyl, dibenzothiophenyl, indazolyl, imidazo [1.2-a]pyridinyl, benzotriazolyl, anthranilyl, 1,2-benzoxazolyl, benzoxazolyl, benzothiazolyl, purinyl, pirydinyl, dipyridylyl, pyrimidinyl, pyrazinyl, 1,3,5-triazinyl, quinolinyl, phthalazinyl, quinazolinyl, and quinoxalinyl.

The terms "alkylheterocyclic" and "arylheterocyclic" refer to radicals formed respectively by the bonding of a substituted or unsubstituted alkyl radical or aryl radical to a heterocyclic radical such that a new radical is generated with the reactive terminus at the alkyl or aryl group.

The term "amino protecting group" as used herein refers to substituents of the amino group commonly employed to block or protect the amino functionality while reaction(s) are carried out at other functional groups of the compound. Examples of such amino-protecting groups include the formyl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl,4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)iso-propoxycarbonyl, 1,1-diphenyleth-1-yloxycarbonyl, 1,1- diphenylprop-1-yloxycarbonyl, 2-phenylprop-2-yloxycarbonyl, 2-(p-toluyl)prop-2-yloxycarbonyl, cyclopentanyloxycarbonyl, 1-methylcylcopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-1-en-3-yloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl, and the like; the benzoylmethylsulfonyl, the 2-(nitro)phenylsulfenyl group, the diphenylphosphine oxide group and like amino protecting groups. The species of amino protecting group employed is not critical so long as the derivatized amino group is stable to the conditions of subsequent reaction(s) on other positions of the molecule and can be removed at the appropriate point without disrupting the remainder of the molecule. Similar amino protecting groups used in the cephalosporin, penicillin, and peptide arts are also embraced by the above terms. Further examples of groups referred to by the above terms are described by J. S. Barton, "Protective Groups in Organic Chemistry", J. G. W. McOmie, Ed., Plenum Press, New York, N.Y., 1973, Chapter 2, and T. W.

Greene, "Protective Groups in Organic Synthesis", John Wiley and Sons, New York, N.Y., 1981, Chapter 7 and T. W. Greene, "Protective Groups in Organic Synthesis", 2nd Ed., John Wiley and Sons, New York, N.Y., 1991. The related term "protected amino" defines an amino group substituted with an amino protecting group discussed above.

The term "carboxy protecting group" as used herein refers to one of the ester derivatives of the carboxylic acid group commonly employed to block or protect the carboxylic acid group while reactions are carried out on other functional groups of the compound. Examples of such carboxylic acid protecting groups include benzyl, 4-nitrobenzyl, 4-methoxybenzyl, 3,4-dimethoxybenzyl, 2,4-dimethoxybenzyl, 2,4,6-trimethoxybenzyl, pentamethylbenzyl, 3,4-methylenediozybenzyl, benzyhydryl, 4,4'-dimethoxybenzhydryl, 2,2,4,4'-tetramethoxybenzhydryl, t-butyl, isobutyl, n-butyl, propyl, isopropyl, ethyl, methyl, t-amyl, trityl, 4-methoxytrityl, 4,4'-dimethoxytrityl, 4,4",4"-trimethoxytrityl, trimethylsilyl, t-butyldimethylsilyl, phenyacyl, 2,2,2-trichloroethyl, p-toluenesulfonylethyl, 4-nitrobenzylsulfonylethyl, allyl, cinnamyl, or 1-(trimethylsilylmethyl)prop-1-en-3-yl, and like moieties. The species of carboxy-protecting group employed is not critical so long as the derivatized carboxylic acid is stable to the conditions of subsequent reaction(s) on other positions of the molecule and can be removed at the appropriate point without disrupting the remainder of the molecule. Carboxy protecting groups similar to those used in the cephalosporin, penicillin, and peptide arts can also be used to protect a carboxy group substituent of the compounds provided herein. Further examples of these groups are found in E. Haslam, "Protective Groups in Organic Chemistry", J. G. W. McOmie, Ed., Plenum Press, .New York, N.Y., 1981, Chapter 5 and T. W. Greene, "Protective Groups in Organic Synthesis", 2nd Ed., John Wiley and Sons, New York, N.Y., 1991, Chapter 5.

The term "etherification" as used herein refers to the linking of organic substituent groups of a molecule by an oxygen atom. For example as in R—O—R wherein each R is an organic substituent and is independently an alkyl, alkenyl, alkynyl, aryl, alkylaryl, aralkyl, alkylheterocycles or heterocycles or subtituted derivative thereof.

The term "prodrugs" as used herein defines derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in.a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, and morpholinoethyl.

The term "α center amino acid protecting group" as used herein refers to a subset of amino protecting groups that is used to protect the amino group in addition to a hydrogen alpha to the amino group from base promoted racemization. Examples of such groups include the trityl group [Cherney, R. J. and Wang, L., *J. Org. Chem.* 61:2544 (1996); Christie, B. D.; Rapoport, H., *J. Org. Chem.* 50:1239 (1985)] and the phenylfluorenyl group [Guthrie, R. D. and Nicolas, E. C., *J. Am. Chem. Soc.* 103:4638 (1981)].

The term "hydroxy activation agent" refers to acid halides, and acid anhydrides that are capable of converting a hydroxyl group into a leaving group labile to base treatment or nucleophilic displacement. Typical hydroxy activation agents include, but are not limited to sulfonating agents such as, methane sulfonyl chloride, p-toluenesulfonyl chloride, phenylsulfonyl chloride, trifluoromethylsulfonyl chloride, and the like, acylating agents such as isobutyl chloroformate, acetyl chloride, and the like, and halogenating reagents such as thionyl chloride, phosphorus tribromide, and the like.

The term "activated hydroxy group" refers to the moiety that results when a compound containing a hydroxy group is reacted with a hydroxy activating reagent e.g. the transformation from O—H to o-methylsulfonyl, o, p-tolunesulfonyl, o-phenylsulfonyl, o-trifluoromethylsulfonyl, o-isobutylacetyl, o-acetyl, chloro, or bromo.

"Pharmaceutically acceptable salt" refers to a salt of the compound of formula I, which is substantially non-toxic to mammals. Typical pharmaceutically acceptable salts include those salts prepared by reaction of the compounds of the present invention with a mineral or organic acid or an organic or inorganic base. Such salts are known as acid addition and base addition salts, respectively. It should be recognized that the particular counter-ion forming a part of any salt of this invention is not of a critical nature, so long as the salt as a whole is pharmaceutically acceptable and as long as the counter-ion does not contribute undesired qualities to the salt as a whole.

Acids commonly employed to form acid addition salts are inorganic acids such as, without limitation, hydrochloric acid, hydrobromic acid, hydriodic acid, sulfuric acid, phosphoric acid, and the like, and organic acids, such as, without limitation, p-toluenesulfonic acid, methanesulfonic acid, oxalic acid, p-bromophenylsulfonic acid, carbonic acid, succinic acid, citric acid, benzoic acid, acetic acid, and the like.

Salts are formed by the addition of base to a compound of formula I. Such base addition salts include those derived from inorganic bases, such as, without limitation, ammonium hydroxide, alkaline metal hydroxides, alkaline earth metal hydroxides, carbonates, bicarbonates, and the like, and organic bases, such as, without limitation, ethanolamine, triethylamine, tris(hydroxymethyl)-aminomethane, and the like. Examples of inorganic bases include, without limitation, sodium hydroxide, potassium hydroxide, potassium carbonate, sodium carbonate, sodium bicarbonate, potassium bicarbonate, calcium hydroxide, calcium carbonate, and the like.

Examples of such pharmaceutically acceptable salts are, without limitation, the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methoxybenzoate, phthalate, sulfonate, xylenesulfonate, phenylacetate, phenylpropionate, phenylbutyrate, citrate, lactate, □-hydroxybutyrate, glycollate, tartrate, methanesulfonate, propanesulfonate, naphthalene-1-sulfonate, naphthalene-2-sulfonate, mandelate, and the like salts of the compound of formula I. The preferred acid addition salts are those formed with mineral acids, such as, without limitation, hydrochloric acid, and hydrobromic acid, and those formed with organic acids, such as, without limitation, maleic acid and methanesulfonic acid. Potassium and sodium salts of compounds of formula I are particularly preferred base addition salts.

"Therapeutically effective amount" means that amount of a compound that will elicit the biological or medical response of a tissue, system, or mammal that is being sought by a researcher or clinician.

Preferred Compounds

A preferred embodiment of this invention is represented by a compound of formula II:

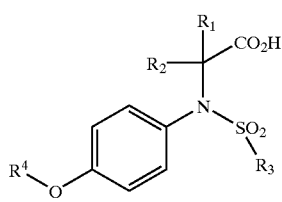

wherein the X of formula (I) is —OR⁴, and R⁴ is a group selected from alkyl, alkenyl, akynyl, aryl, aralkyl, alkyaryl, alkyl heterocyclic, arylheterocyclic radical or a pharmaceutically acceptable salt or prodrug thereof.

More preferred are the compounds of formula II wherein R⁴ is aryl, alkylaryl, arylalkyl, heterocyclic or alkylheterocyclic radical or a pharmaceutically acceptable salt or pro-drug thereof. Examplary of the poreferrred compounds is a compound represented by the formula (IIa)

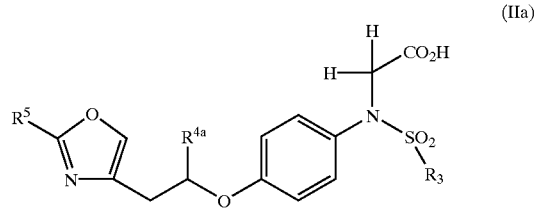

wherein $R^{4}a$ is hydrogen, $C_1$ to $C_4$ alkyl, $C_1$ to $C_4$ alkenyl or combines with the phenyl ring to form a 5 membered (i.e., benzofuran) or 6 membered (i.e., benzopyran)ring with the oxygen atom.

Most preferred is a compound of formula III:

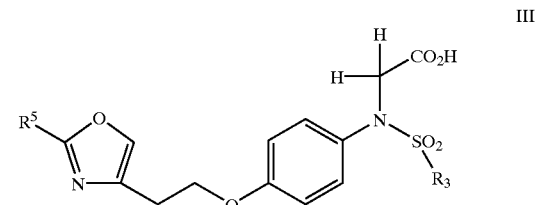

wherein $R^5$ is H, $C_1$–$C_8$ alkyl, phenyl or an aryl group and $R^3$ is as defined supra.

Particularly preferred is a compound selected from the group consisting of:

N-[4-(2-(Phenyloxazol-4yl)ethoxy)phenyl]-N-isopropyl sulfonylglycine represented by the formula:

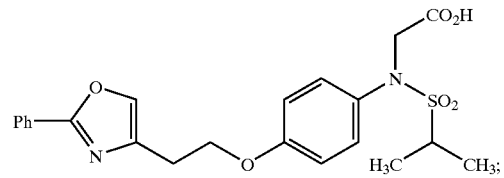

N-4[-(2-(Phenyloxazol-4yl) ethoxy)phenyl]-N-methylsufonyl-glycine represented by the formula:

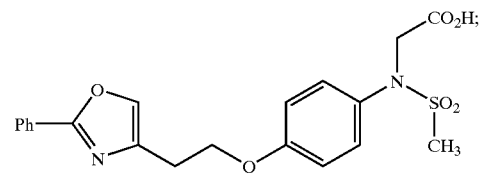

N-[4-(2-(Phenyloxazol-4yl)ethoxy)phenyl]-N-N'N'-dimethyl aminosulfonylglycine represented by the formula:

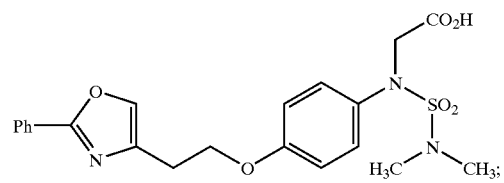

N-[4-(2-(Phenyloxazol-4yl)ethoxy)phenyl]-N-phenylmethyl sulfonylglycine represented by the formula:

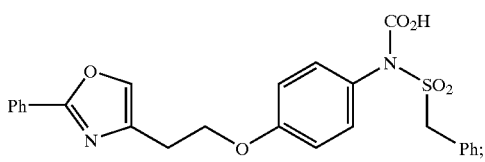

and, N-[5-(2-(2-Naphthylmethyl)benzofuranyl)]-N-methylsufonyl glycine

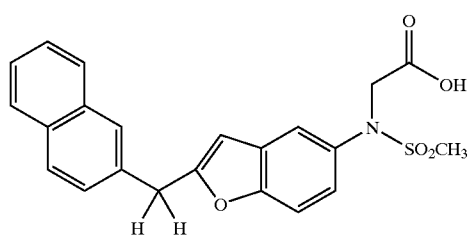

Intermediates and salts of compounds of formula I are also objects of this invention. An examples of a salt includes but is not limited to the following:

sodium N-[4-(2-phenyloxazol-4yl-ethoxy)phenyl]-N-sulfonylmethyl Glycinate represented by the formula:

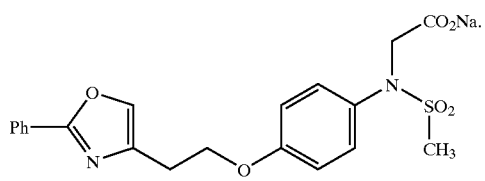

The compounds of formula I are readily prepared by sulfonylation of substituted anilines with variously substituted sulfonyl halides such as methanesulfonyl chloride in an inert solvent such as THF, $CH_2Cl_2$ and the like, with or without external cooling as required to moderate the vigor of the reaction. Reactions are generally conducted in a temperature range of 0° C.–50° C. in the presence of a base such as pyridine, triethylamine or the like. The substituted anilines may be obtained by procedures described in the literature or synthesized as required by a scheme such as exemplified in Scheme 1 outlined below.

Scheme 1

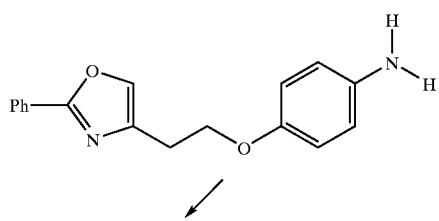

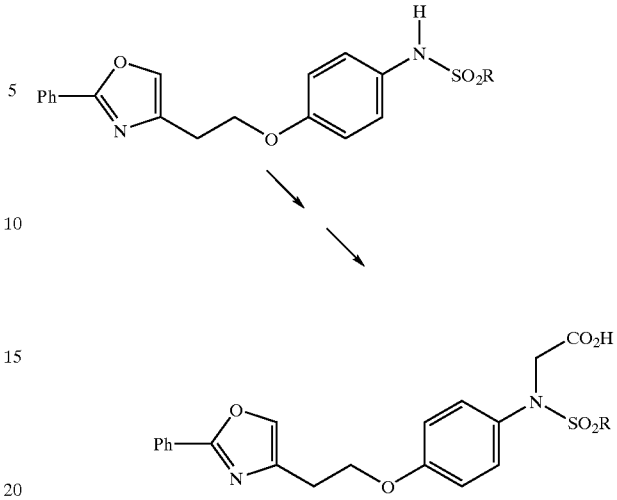

The substituted sulfonyl halides may be obtained by purchase or prepared by methods described in the literature. The resulting sulfonamides may be alkylated with alkyl halides containing a carboxyl group protected in some suitable way such as its ester, such as methyl bromoacetate. The alkylations may be conducted in an inert solvent such as methylethylketone, in the presence of a base such potassium carbonate, at a temperature such as 80° C. and in the presence of a catalyst such as KI so as to allow the reaction to proceed at a convenient rate. The initial alkylation products need not be isolated but subjected to deprotection procedures, such as base catalyzed hydrolysis, to provide the subject acids of the present invention.

A substituted aniline for the compounds of formula I wherein the group X is attached to the N-phenyl ring at the 3 and 4 position to form the benzofuran ring system for example, may be prepared by a process such as the following:

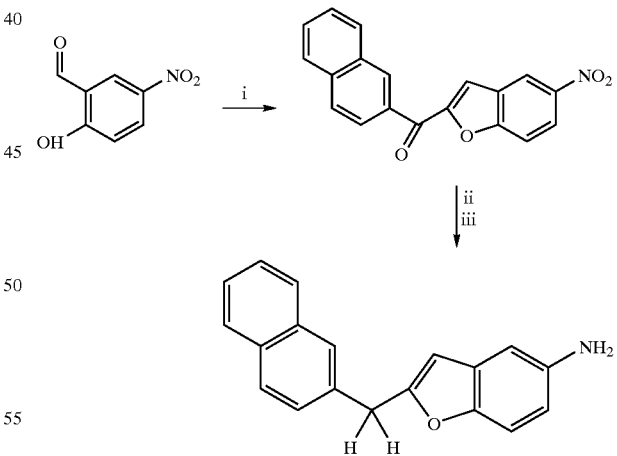

In this procedure, a solution of a 5-nitro-2-hydroxy benzaldehyde dissolved in a protic solvent for example, dimethylformamide (DMF) was reacted with 2-bromo-2'-acetophenone or other suitably substituted 2-halo acetophenone compound. The reaction (step i) was effected by the addition of a base such as for example powdered potassium carbonate; and catalyzed by addition of an iodide source for example potassium iodide or sodium iodide, etc. The reaction mixture was maintained at 40to 80° C. but preferably at 55° C. for 1 to 10 hours, preferably 3 hours.

The product mixture was diluted with water and the crystals were filtered after standing at room temperature from 2 to 24 hours. In a second step (ii) the carbonyl group from the product of step is reduced to the methylene group using sodium borohydride in methanol or other suitable ketone reducing agents. The nitro group of the step (ii) reaction product is further reduced to the amine by hydrogenation techniques such as hydrogenation in the presence of palladium on carbon in an acetic acid/ethanol solution. Procedures for hydrogenation are well known to one of skill in the art. One skilled in the art is also aware that depending on the substrate steps (ii) and (iii) may be combined into a single step or operation to obtain the target substituted aniline compound.

Alternatively the substituted aniline may be prepared by reacting the group $R^4X$ wherein $R^4$ is as defined above and X is a leaving group such as a halo group, preferably, bromo, with the corresponding nitrophenol or substituted nitrophenol to form the etherified product B as shown in Scheme 3:

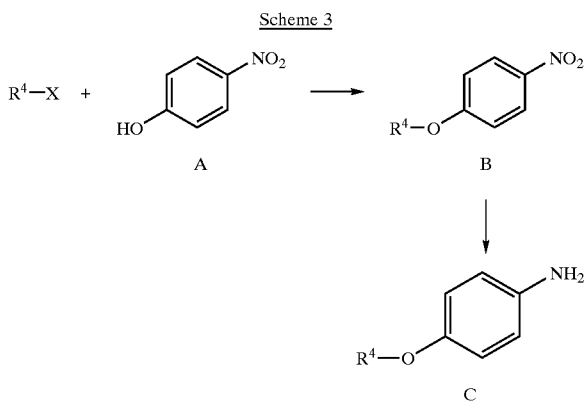

The etherification reaction is preferably performed by phase transfer catalysis using tetrabutylammonium bromide (TBAB) and sodium hydroxide in a mixture of methylene chloride and water. The etherification reaction is performed at reflux for 2 to 48 hours preferably 24 hours, and the product (B) obtained after isolation, is preferably purified by chromatography.

The etherification product B is reduced by any of well known nitro group reduction techniques for example palladium catalyzed hydrogenation to afford the corresponding aniline (C).

The substituted aniline produced by either of the above procedure or other known procedure is then subjected to the general process of Scheme 1 to produce compounds of the present invention.

Formulation

The compounds of the present invention can be administered in oral forms, such as tablets, capsules, pills, powders, granules, elixirs, tinctures, suspensions, syrups, and emulsions. They may also be administered in parenteral forms, such as intravenous (bolus or infusion), intraperitoneal, subcutaneous, intramuscular, and the like. forms, well known to those of ordinary skill in the pharmaceutical arts. The compounds of the present invention can be administered in intranasal form via topical use of suitable intranasal vehicles, or via transdermal routes, using transdermal delivery systems well-known to those of ordinary skill in that art.

A dosage regimen utilizing the compounds of the present invention is selected by one of ordinary skill in the medical or veterinary arts in view of a variety of factors, including without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

The compounds of the present invention are preferably formulated prior to administration together with one or more pharmaceutically acceptable excipients. Excipients are inert substances such as, without limitation, carriers, diluents, flavoring agents, sweeteners, lubricants, solubilizers, suspending agents, binders, tablet disintegrating agents and encapsulating material.

Therefore, yet another embodiment of the present invention is a pharmaceutical formulation comprising a compound of the invention and one or more pharmaceutically acceptable excipients that are compatible with the other ingredients of the formulation and not deleterious to the recipient thereof. Pharmaceutical formulations of the invention are prepared by combining (e.g., mixing) a therapeutically effective amount of the compounds of the invention together with one or more pharmaceutically acceptable excipients therefor. In making the compositions of the present invention, the active ingredient may be admixed with a diluent, or enclosed within a carrier, which may be in the form of a capsule, sachet, paper, or other container. The carrier may serve as a diluent, which may be solid, semi-solid, or liquid material which acts as a vehicle, or can be in the form of tablets, pills, powders, lozenges, elixirs, suspensions, emulsions, solutions, syrups, aerosols (as a solid or in a liquid medium), ointments, containing, for example, up to 10% by weight of the active compound, soft and hard gelatin capsules, suppositories, sterile injectable solutions and sterile packaged powders.

For oral administration in the form of a tablet or capsule, the active ingredient may be combined with an oral, non-toxic, pharmaceutically acceptable carrier, such as without limitation, lactose, starch, sucrose, glucose, methyl cellulose, calcium carbonate, calcium phosphate, calcium sulfate, sodium carbonate, mannitol, sorbitol and the like; together with, optionally, disintegrating agents, such as, without limitation, maize, starch, methyl cellulose, agar, bentonite, xanthan gum, alginic acid, and the like; and optionally, binding agents, for example, without limitation, gelatin, acacia, natural sugars, betalactose, corn sweeteners, natural and synthetic gums, acacia, tragacanth, sodium alginate, carboxymethylcellulose, polyethylene glycol, waxes, and the like; and optionally, lubricating agents, for example, without limitation, magnesium stearate, sodium stearate, stearic acid, sodium oleate, sodium benzoate, sodium acetate, sodium chloride, talc, and the like.

In powders, the carrier is a finely divided solid which is in admixture with the finely divided active ingredient. In tablets, the active ingredient is mixed with a carrier having the necessary binding properties in suitable proportions and compacted in the shape and size desired. The powders and tablets preferably contain from about 1 to about 99 weight percent of the active ingredient which is the novel composition of the instant invention. Suitable solid carriers are magnesium carbonate, magnesium stearate, talc, sugar, lactose, pectin, dextrin, starch, gelatin, tragacanth, methylcellulose, sodium carboxymethyl cellulose, low melting waxes, and cocoa butter.

Sterile liquid formulations include suspensions, emulsions, syrups, and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

Preferably, the pharmaceutical formulation is in unit dosage form. A "unit dosage form" is a physically discrete unit containing a unit dose, suitable for administration in human subjects or other mammals. A unit dosage form can be a capsule or tablet, or a number of capsules or tablets. A "unit dose" is a predetermined quantity of the active compound of the present invention, calculated to produce the desired therapeutic effect, in association with one or more pharmaceutically acceptable excipients. The quantity of active ingredient in a unit dose may be varied or adjusted from about 0.1 to about 1000 milligrams or more according to the particular treatment involved. It may be appreciated that it may be necessary to make routine variations to the dosage depending on the age and condition of the recipient. The dosage will also depend on the route of administration.

The oral route is most preferred. Typical oral dosages of the present invention, when used for the indicated effects, will range from about 0.01 mg per kg body weight per day (mg/kg/day) to about 50 mg/kg/day, preferably from 0.1 mg/kg/day to 30 mg/kg/day, and most preferably from about 0.5 mg/kg/day to about 10 mg/kg/day. The compounds of the present invention may be administered in a single daily dose, or the total daily dose may be administered in divided doses, two, three, or more times per day. Where delivery is via transdermal forms, of course, administration is continuous.

The human to whom the compounds and formulations of the present invention are administered is afflicted with a disease or condition in which blood glucose levels are not adequately controlled without medical intervention, but wherein there is endogenous insulin present in the human's blood and or afflicted with a disease or condition wherein lipid levels are not adequately or desirably controlled as in hyperlipidemia. Non-insulin dependent diabetes mellitus (NIDDM) is a chronic disease or condition characterized by the presence of insulin in the blood, even at levels above normal, but resistance or lack of sensitivity to insulin action at the tissues. The compounds and formulations of the present invention are also useful to treat acute or transient disorders in insulin sensitivity, such as sometimes occur following surgery, trauma, myocardial infarction, and the like. The compounds and formulations of the present invention are also useful for lowering serum triglyceride levels. Elevated triglyceride level, whether caused by genetic predisposition or by a high fat diet, is a risk factor for the development of heart disease, stroke, and circulatory system disorders and diseases. The physician of ordinary skill will know how to identify humans who will benefit from administration of the compounds and formulations of the present invention.

The following formulation examples are illustrative only and are not intended to limit the scope of the invention in any way.

Formulation 1

Hard gelatin capsules are prepared by mixing the following ingredients and filling the mixture, in 460 mg quantities, into hard gelatin capsules.

| Ingredient | Quantity (mg/capsule) |
|---|---|
| Active ingredient | 250 |
| Starch, dried | 200 |
| Magnesium stearate | 10 |
| Total | 460 |

Formulation 2

A tablet containing 250 mg of the compound of the present invention is prepared by blending the components listed below and then compressing 665 mg of the blend into a tablet.

| Ingredient | Quantity (mg/tablet) |
|---|---|
| Active ingredient | 250 |
| Cellulose, microcrystalline | 400 |
| Silicon Dioxide, fumed | 10 |
| Stearic Acid | 5 |
| Total | 665 |

Formulation 3

A tablet containing 60 mg of the compound of the present invention is prepared as follows:

| Ingredient | Quantity (mg/tablet) |
|---|---|
| Active ingredient | 60 |
| Starch | 45 |
| Cellulose, microcrystalline | 35 |
| Polyvinylpyrrolidone, 10%, aqueous | 4 |
| Sodium carboxymethyl starch | 4.5 |
| Magnesium stearate | 0.5 |
| Talc | 1 |
| Total | 150 |

The active ingredient, starch, and cellulose are passed through a No. 45 mesh U.S. sieve and mixed thoroughly. The solution of polyvinylpyrrolidone is mixed with the resultant powders and then passed through a No. 14 mesh U.S. sieve. The granules so produced are dried at 50° C. and passed through a No. 18 mesh U.S. sieve. The sodium carboxylmethyl starch, magnesium stearate, and talc, previously passed though a No. 60 mesh U.S. sieve, are then added to the granules which, after mixing, are compressed on a tablet machine to yield tablets each weighing 150 mg.

Formulation 4

Capsules containing 80 mg of the active compound of the present invention are made as follows:

| Ingredient | Quantity (mg/capsule) |
| --- | --- |
| Active ingredient | 80 |
| Starch | 59 |
| Cellulose, microcrystalline | 59 |
| Magnesium stearate | 2 |
| Total | 200 |

The active ingredient, starch, cellulose, and magnesium stearate are blended, the blend is passed through a No. 45 mesh U.S. sieve, and then hard gelatin capsules are filled with 200 mg of the blend.

Formulation 5

Suppositories each containing 225 mg of active compound of the present invention are made as follows:

| Ingredient | Quantity (mg/suppository) |
| --- | --- |
| Active ingredient | 225 |
| Saturated fatty acid glycerides | 2,000 |
| Total | 2,225 |

The active compound is passed through a No. 60 mesh U.S. sieve and suspended in the saturated fatty acid glycerides, previously melted using the minimum heat necessary. The mixture is then poured into a suppository mold of nominal 2 g capacity and allowed to cool.

Formulation 6

Suspensions each containing 50 mg of active compound of the present invention per 5 mL dose are made as follows:

| Ingredient | Quantity per dose |
| --- | --- |
| Active ingredient | 50 mg |
| Sodium Carboxymethyl Cellulose | 50 mg |
| Syrup | 1.25 mL |
| Benzoic Acid Solution | 0.10 mL |
| Flavor | q.v. |
| Color | q.v. |
| Purified Water to total volume: | 5 mL |

The active ingredient, starch, cellulose, and magnesium stearate are blended, the blend is passed through a No. 45 mesh U.S. sieve, and then hard gelatin capsules are filled with 200 mg of the blend.

Formulation 7

An intravenous formulation may be prepared as follows:

| Ingredient | Quantity |
| --- | --- |
| Active ingredient | 100 mg |
| Sterile, isotonic saline | 1000 mL |

The compound of the present invention is dissolved in the saline and administered intravenously at a rate of 1 mL per minute to a subject in need thereof.

Formulation 8

An aerosol solution is prepared by mixing the active ingredient with ethanol and then with the propellant 22, cooled to −30° C., and transferred to a filling device. The required amount is then fed to a stainless steel container and diluted with the remainder of the propellant. The valve units are finally fitted to the container.

| Ingredient | Weight % |
| --- | --- |
| Active ingredient | 0.25 |
| Ethanol | 29.75 |
| Propellant 22 | 70.00 |
| Total | 100.00 |

Demonstration of Hypoglycemic Efficacy

Male obese-diabetic viable yellow (AvY) mice were divided into two groups of 6 each. One group was fed repelletized purina 5008 Chow and the second group was fed repelletized Purina 5008 Chow, admixed with varying doses of the candidate compound. Blood samples were taken before the experiment was initiated and 7 and 14 days after initiation. Body weight and food consumption were monitored. The blood glucose level after 7 or 14 days of treatment was measured and recorded as a percent of the initial value, compared to the untreated control (first) group. The results are presented in the table 1 below; and include the dose of the candidate compound as a weight percent of the amount incorporated into the diet. Also in the table is a representative value for a positive control (a known hypoglycemic agent reported by a Takeda group [J. Med. Chem., 35, 2617]) administered in the same way as a canditate compound of the present invention.

TABLE 1

| Example No. | Dose | % BG14 (BG0 = 100) |
| --- | --- | --- |
| 1 | .03 | 53.1 |
| 2 | .03 | 76.4 |
| 3 | .03 | 57.9 |
| 4 | .03 | 70.1 |
| 5 | .03 | 77.0 |
| 6 | .03 | 93.1 (day 7) |
| Takeda | .003 | 29.0 |

BG means blood glucose level; BG0 means blood glucose level at day zero and BG14 means blood glucose level at day 14 accordingly.

Experimental-General

Melting points were measured using a Thomas Hoover capillary instrument and are uncorrected. Ratios are on a weight basis, except fluid mixtures for chromatography, which are on a volume basis. Temperatures are in degrees Celsius. Chromatography was performed on silica under low or medium pressure "flash" conditions as described by C. W. Still, et al., *J. Org. Chem.* 43:2923 (1978). Thin Layer Chromatography (TLC) was performed on glass plates coated with selica gel, 240 microns, grade 2.

Proton NMR spectra were obtained using at 300.15 MHz and peak positions are reported as delta values relative to an internal TMS standard.

The following abbreviations for common solvents, reagents and substituent groups are used throughout:

h, hour(s)

rt, room temperature (ca. 250)

mM, millimole(s)

mL, milliliters

MeOH, methanol

EtOH, ethanol

THF, tetrahydrofuran

NaH, sodium hydride

EtOAc, ethyl acetate

HOAc, acetic acid

DMF, Dimethyl formamide

Bz, benzoyl

Ac, acetyl

Synthetic Intermediates

4-[2-(2-Phenyl-4-oxazolyl)ethoxy]aniline was prepared by the method described by T. Shoda, K. Mizuno, Y. Momose, H. Ikeda, T. Fujita and K. Meguro (*J. Med. Chem.* 1992, 35, 2617–2626).

EXAMPLE 1

N-[4-(2-(Phenyloxazol-4yl)ethoxyl]phenyl)-N-isopropyl Sulfonylglycine

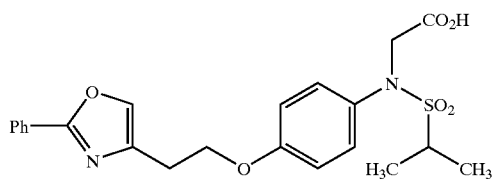

Part A. Preparation of N-(4-(2-Phenyl-4-oxazolylethoxy) phenyl) isopropyl Sulfonamide.

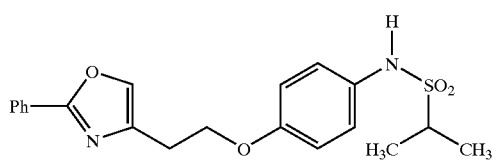

A stirred solution of 2.8 g (10 mM) of 4-[2-(2-Phenyl-4-oxazolyl)ethoxy]aniline in 30 mL of THF was cooled in an ice bath and treated with 5 mL of pyridine, followed by 3 mL of isopropyl sulfonyl chloride. The resulting mixture was stirred in the ice bath 3h and allowed to warm to rt over night. The thick red mixture was treated with 300 mL of $H_2O$ and the precipitated red power filtered, washed with $H_2O$ and dried. Dissolution in $CH_2Cl_2$, followed by flash chromatography, afforded crude product which crystallized as needles, mp 99–101BC, from $CH_2Cl_2$-Hexane. Yield 1.05 g (27%). Anal. Cal. For $C_{20}H_{22}N_2O_4S$ (MW 386): C, 62.16; H, 5.73; N, 7.25. Found: C, 62.42; H, 5.85; N 7.35. MS: m/e 386. NMR (CDCl$_3$) 1.4 d (6H, J=2); 3.1 t(2H); 3.2 heptet (1H); 4.3 t(2H); 6.1 s(1H, exchanges with D$_2$O); 6.9 d(2H, J=1); 7.1 d(2H, J=1); 7.55 m(3H), 7.6 s(1H); 8.0 m(2H).

Part B. Preparation of N-[4-(2-(Phenyloxazol-4yl)ethoxy) phenyl]-N-isopropylsulfonylglycine.

A stirred solution of 1.83 g of the intermediate prepared in Part A and 20 mL of MEK was treated with 1g of powdered KI, 4.5 g of powdered K$_2$CO$_3$, 1.5 mL of methyl bromoacetate and heated to reflux for 5h. The cooled mixture was treated with 200 mL of H$_2$O and extracted with a total of 150 mL EtOAc in 3 portions. The combined extracts were evaporated in vacuo and the oily residue taken up in 20 mL of MeOH. The resulting solution was treated with 10 mL of 2N NaOH, refluxed 2 h, cooled and the pH adjusted to 2 with 5N HCl. The resulting mixture was cooled and the precipitated solid washed with H$_2$O. Recrystallization of the solid from i-PrOH afforded 0.9 g (43%) of the product as fluffy tan needles, mp 136–139° C. Anal. Cal. for $C_{22}H_{24}N_2O_6S$ (MW 444): C, 59.45 H, 5.44; N, 6.30. Found: C, 59.22; H, 5.53; N, 6.05; IR(KBr) 3500, 1705 cm$^{-1}$; NMR: (CDCl$_3$) 1.4 d(6H, J=2); 3.1 t(2HO; 3.2 heptet(1H); 4.3 t(2H); 4.45, s(2H); 6.9 d(2H, J=1); 7.1 d(2H, J=1); 7.55 m(3H), 7.6 s(1H); 8.0 m(2H). MS: m/e 444.

EXAMPLE 2

N-4[-(2-(Phenyloxazol-4yl)ethoxy)phenyl]-N-methylsufonyl-glycine

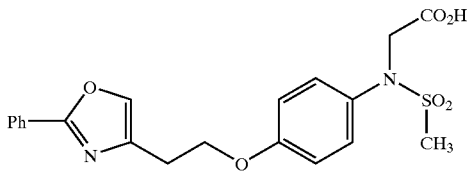

Part A. Preparation of N-(4-(2-Phenyl-4-oxazolylethoxy) phenyl) methyl Sulfonamide

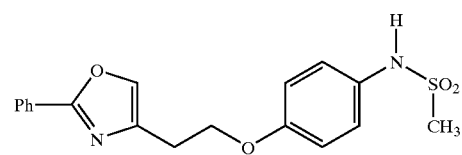

The procedure of Example 1, Part A was duplicated, substituting methanesulfonyl choride for isopropylsulfonyl chloride to provide a 72% yield of product as white flakes mp 134–137° C. after recrystallization from i-PrOH containing 10% THF and treatment with decolorizing charcoal. Anal. Cal. For $C_{18}H_{18}N_2O_4S$ (MW 358): C, 60.32; H, 5.06; N 7.82. Found: C, 60.23; H, 5.14; N, 7.80. MS: m/2 358. NMR: (CDCl$_3$) 2.95 s (3H); 3.1 t(2H); 4.3 t(2H); 6.35 s(1H, exchanges with D$_2$O); 6.9 d(2H, J=1); 7.1 d(2H, J=1); m(3H), 7.6 s(1H); 8.0 m(2H).

Part B. Preparation of N-4[-(2 -(Phenyloxazol-4yl) ethoxy)phenyl]-N-methylsufonyl-glycine.

The compound prepared in Part A was treated according to the procedure of Example 1, Part B to afford a 28% yield of product as white needles mp 200–201° C. after crystallization from THF-i-PrOH. Anal. Cal. For $C_{20}H_{20}NO_6S$; (MW 416): C, 57.68; H, 4.84; N, 6.73. Found: C, 57.41; H, 4.90; N, 6.55.

MS: m/e 416. IR (KBr): 3139, 1715 cm$^{-1}$. NMR: (CDCl$_3$) 1.6 bs (1H, exchanges with D$_2$O); 3.10 s (3H); 3.15 t(2H);4.3 t(2H); 4.4 s (2H); 6.9 d(2H, J=1); 7.1 d(2H, J=1) 7.55 m(3H) , 7.6 s(1H); 8.0 m(2H).

EXAMPLE 3

Sodium N-(4-(2-Phenyl-4-oxazolylethoxy)phenyl)-N-methylsulfonylglycinate

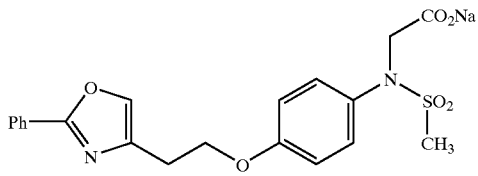

A stirred solution of 4.62 g of the intermediate prepared as in Example 2, Part A, 30 mL MEK, 2.5 mL methyl bromoacetate, 0.7 g of powdered KI and 4 g of powdered $K_2CO_3$ was refluxed for 5 h. The cooled mixture was diluted with 250 mL of $H_2O$ and extracted with 100 mL EtOAc in 3 portions. The combined exracts were washed with $H_2O$ and evaporated in vacuo. The residue was dissolved in 300 mL MeOH, the solution treated with 20 mL of 2N NaOH and stirred at reflux 2 h. The hot solution was treated with decolorizing charcoal and filtered. On cooling, the filtrate deposited an off-white powder. One gram of this powder was recrystallized twice from MeOH to provide 0.82 g of product as fluffy white needles mp 232–234BC (dec) Anal. Cal. For $C_{22}H_{23}N_2O_6SNa$: C, 56.64; H, 4.97; N, 6.00. Found: C, 56.80; H, 5.04; N, 6.13. IR (KBr): 3498 broad, 1601 broad $cm^{-1}$.

EXAMPLE 4

N-[4-(2-(Phenyloxazol-4yl)ethoxy)phenyl]-N-N'N'-dimethyl aminosulfonylglycine

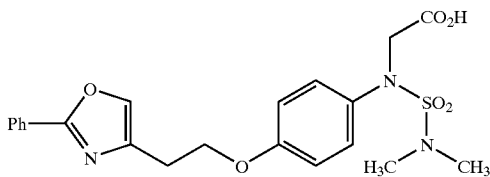

A solution of 2.8 g of 4-[2-(2-phenyl-4-oxazolyl)ethoxy] aniline in 30 mL THF cooled in an ice bath was treated with 2 mL $Et_3N$ and 5 mL of N,N-dimethylsulfamoyl chloride. The fuming mixture was warmed to room temperature and stirred for 6h. The mixture was treated with 250 mL 5N HCl and extracted with 150 mL EtOAc in 3 portions. The combined extracts were washed with $H_2O$, brine, dried with $MgSO_4$ and evaporated in vacuo to provide a brown oil which partially solidified on trituration with hexane. This material was dissolved in 20 mL MEK, treated with 1.4 mL methylbromoacetate, 0.7 g powdered KI, 2 g powdered $K_2CO3$ and the stirred mixture heated to reflux 3 h. After stirring overnight at rt, the reaction product was then acidified with HCl before being worked up by the procedure of Example 1 Part B to afford an initial product as a dark red sludge. Repeated recrystallization from i-PrOH/Hexane afforded 1.0 g (22%) of pure product as nearly white needles mp 154–156° C. Anal. Cal. For $C_{21}H_{23}NO_6S$ (MW 445): C, 56.62; H, 5.20 N, 9.43. Found: C, 56.68; H, 5.38; N, 9.19. MS: m/e 445 NMR: ($CDCl_3$) 2.8 s (6H), 3.1 t(2H), 4.5 t(2H), 4.5 s (2H), 6.9 d(2H, J=1); 7.1 d(2H, J=1); 7.55 m(3H), 7.6 s(1H); 8.0 m(2H).

EXAMPLE 5

N-[4-(2-(phenyloxazol-4yl)ethoxy)phenyl]-N-phenylmethyl sulfonylglycine

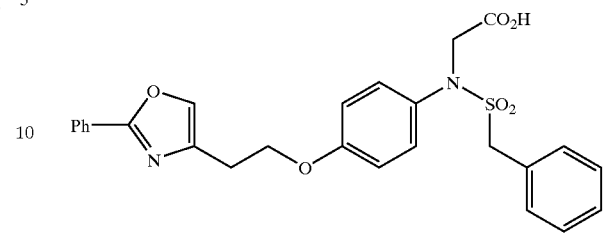

The procedure of example 4 using 2.4 g of 4-[2–2(2-phenyloxazo-4yloethoxy)aniline and 1.9 g of toluenesulfonylchloride afforde 0.7 g (16%) of product mp 147–149° C. after several recrystallizations from MeOH/i-$Pr_2O$. Anal. Calc. For $C_{26}H_{24}N_2O_6S$ (mw 492): C, 63.40; H, 4.91; N, 5.69. Found: C, 63.68; H, 5.00; N, 5.75. MS: m/e 492.

EXAMPLE 6

N-[5-(-2-(2-naphthylmethyl)benzofuranyl)]-N-methylsulfonylglycine

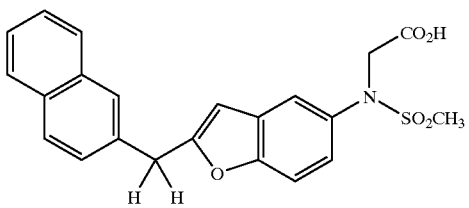

Part A. Preparation of (2-naphthyl) [2-(5-nitro) benzofuranyl] ketone

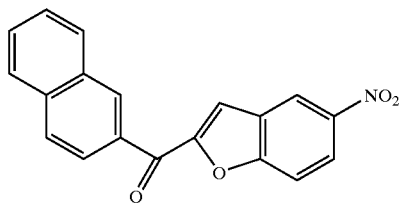

A stirred solution of 16.71 9 of 5-nitro-2-hydroxy benzaldehyde in 100 mL of DMF was warmed to 55° C. in water bath and treated with 24.91 g of 2-bromo-2'-acetonaphthone, 1.4 g of powdered KI, and 28.3 g of powdered $K_2CO_3$. The resulting pale yellow-brown mixture was warmed at 68–74° C. for 1 h during which time an initially formed solid had largely re-dissolved, to be replaced by a thick precipitate. An additional 50 mL/DMF was added to facilitate stirring, the mixture kept at 68–72° C. for an additional 2 h, treated with 1000 mL $H_2O$ and allowed to stand overnight in the refrigerator. The cooled mixture was filtered, the tan solid washed thoroughly with $H_2O$ and dried. Recrystallization from DMF/i-PrOH afforded 27.6 g (87%) of product as tan flakes mp 209–212° C. Anal. Cal. For $C_{19}H_{11}NO_4$ (MW 317): C, 71.92; H, 3.49; N, 4.41. Found: C, 72.08; H, 3.53; N, 4.53.

Part B. Preparation of N-methylsulfonamido 2-(2-naphthylmethyl)-5-amino benzofuran

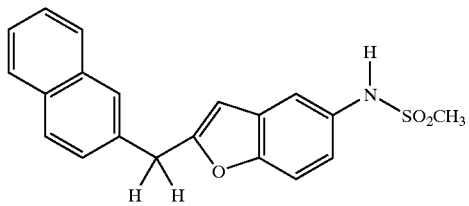

A stirred mixture 6.34 g of the intermediate prepared in Part A, 50 mL, THF and 50 mL of MeOH was cooled in an ice bath and treated with a total of 0.85 g $NaBH_4$ in 3 portions. The mixture was stirred in the ice bath 2 h, allowed to warm to room temperature and stirred an additional 1 h. Solvents were partially removed in vacuo, the residue treated with 200 mL $H_2O$ and the mixture extracted with 150 mL EtOAc in 4 portions. The combined extracts were washed with $H_2O$, brine, dried over $MgSO_4$ and evaporated to provide 6.30 g of a light brown taffy. This material was subjected to catalytic hydrogenation/hydrogenolysis, using EtOH containing 0.1 mL $H_2SO_4$ as solvent, 5% Pd/C as catalyst and a reaction time of 8h at rt. The combined solvent/catalyst mixture was treated with 2N NaOH to pH 10, stirred thoroughly and filtered. The filtrate was evaporated in vacuo and the residue dissolved in 200 mL EtOAc. The solution was washed with $H_2O$, brine, dried over $Na_2SO_4$ and evaporated to a red-brown oil which solidified on trituration with cold EtOH to provide 3.67 g of red-brown crystals mp 88–91° C. A sample of 2.1 g of this solid dissolved in 25 mL of THF was cooled in an ice bath and treated with 5 mL of pyridine, followed by 2 mL of methanesulfonyl chloride. After 5 h, TLC showed consumption of starting material. The mixture was treated with 200 mL 2N HCl and stirred overnight. The mixture was extracted with 200 mL EtOAC in 4 portions. The dark extracts were washed with $H_2O$, brine, dried over $MgSO_4$ and filtered through a short column of silica. Evaporation of the eluates and crystallization of the residue from EtOAC/i-PrOH provided 1.1 g (41%) of product as red-tan powder mp 158–160° C. Anal. Cal. For $C_{20}H_{17}NO_3S$ (MW 351): C, 68.36; H, 4.88; N, 3.99. Found: C, 68.42; H, 5.15; N, 3.75. MS: m/e 351.

Part C. Preparation of N-[5-(-2-(2-naphthylmethyl)benzofuranyl)]-N-methylsulfonylglycine A stirred solution of the intermediate prepared in Part B in 40 mL of MEK was treated with 0.6 g of powdered KI, 2.0 g of powdered $K_2CO3$, 0.7 mL methyl bromoacetate and heated to reflux for 5 h. The cooled mixture was treated with 300 mL $H_2O$ and extracted with a total of 150 mL EtOAc in 3 portions. The combined extracts were washed with $H_2O$, brine, and evaporated to a yellow-brown oil. The residue was dissolved in 20 mL of MeOH, the solution treated with 1 mL of 2N NaOH and heated to reflux for 2 h. After stirring overnight at rt, the solution was acidified with HCL and the resulting mixture extracted with 125 mL EtOAC in 3 portions. The combined extracts were washed with $H_2O$, brine, dried with $MgSO_4$ and evaporated to an oil which slowly crystallized on trituration with cold i-PrOH. Recrystallization from the THF/Hexane provided 0.65 g (51%) of product as fine tan crystals mp 160–165° C. (dec). Anal. Cal. For $C_{22}H_{19}NO_5S$ (MW 409): C, 56.64; H, 4.97; N, 6.00. Found: C, 56.80; H, 5.04; N, 6.13. Ms: mi/e 409.

What is claimed is:

1. A compound of formula I:

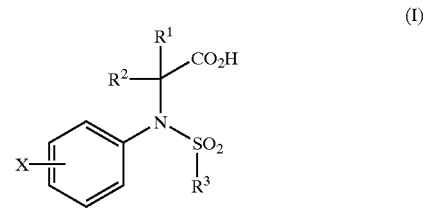

wherein, $R^1$, $R^2$, and $R^3$ independently represent hydrogen, alkyl, alkenyl, alkynyl, aryl, or aralkyl groups having 1 to 8 carbon atoms;

X represents an alkoxyalkyl, alkoxyaryl, alkoxyalkylaryl, aralkylalkoxy, or alkoxyalkylheterocycle; or a pharmaceutically acceptable salt or prodrug thereof.

2. The compound according to claim 1 depicted by formula II:

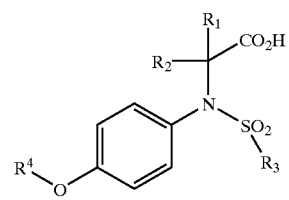

wherein the X of formula (I) is $OR^4$, and $R^4$ is a group selected from aryl, aralkyl, alkyaryl, alkylheterocyclic, or alkylarylheterocyclic; or a pharmaceutically acceptable salt thereof.

3. The compound according to claim 1 wherein X is the group 2-Phenyl-4-oxazolylethoxy, $R^1$ and $R^2$ are hydrogen and $R^3$ is selected from the group consisting of alkyl, aryl, aralkyl, and alkylaryl.

4. A compound selected from the group consisting of:

N-[4-(2-(Phenyloxazol-4yl)ethoxy)phenyl]-N-isopropyl sulfonylglycine represented by the formula:

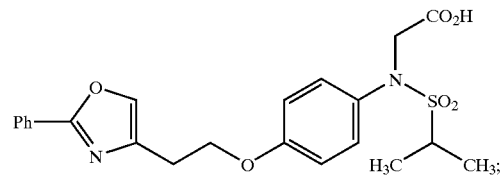

N-4[-(2-(Phenyloxazol-4yl)ethoxy)phenyl]-N-methylsufonyl-glycine represented by the formula:

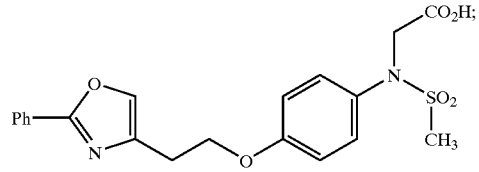

N-[4-(2-(Phenyloxazol-4yl)ethoxy)phenyl]-N-N'N'-dimethyl aminosulfonylglycine represented by the formula:

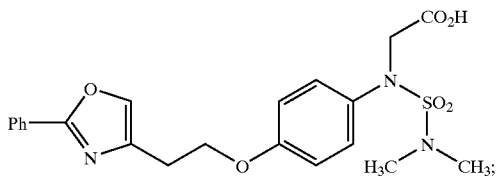

N-[4-(2-(Phenyloxazol-4yl)ethoxy)phenyl]-N-phenylmethyl sulfonylglycine represented by the formula:

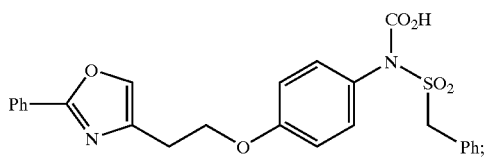

and,

N-[5-(2-(2-Naphthylmethyl)benzofuranyl)]-N-methylsufonyl glycine

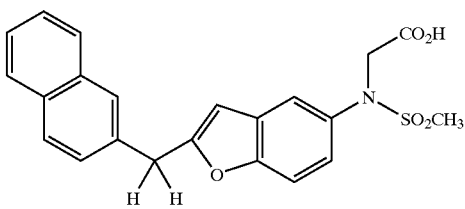

or a pharmaceutically acceptable salt or prodrug thereof.

5. A pharmaceutical formulation comprising as an active ingredient the compound of formula (I), as claimed in any one of claims 1 to 3, together with one or more pharmaceutically acceptable excipients.

6. A method of treating hyperglycemia in a mammal in need thereof comprising administering to a mammal in need thereof an effective amount of the compound of claim 1.

7. A method of treating hyperlipidemia in a mammal in need thereof comprising administering to said mammal an effective amount of the compound of claim 1.

8. A method of treating hyperglycemia comprising administering to a mammal in need thereof an effective amount of the compound of claim 3.

9. A method of treating hyperlipidemia comprising administering to a mammal in need thereof an effective amount of the compound of claim 3.

* * * * *